(12) United States Patent
Gill

(10) Patent No.: US 10,369,329 B2
(45) Date of Patent: Aug. 6, 2019

(54) NEUROSURGICAL APPARATUS AND METHOD

(71) Applicant: RENISHAW PLC, Wotton-under-Edge, Gloucestershire (GB)

(72) Inventor: Steven Streatfield Gill, Bristol (GB)

(73) Assignee: RENISHAW PLC, Wotton-under-Edge (GB)

(*) Notice: Subject to any disclaimer, the term of this patent is extended or adjusted under 35 U.S.C. 154(b) by 859 days.

(21) Appl. No.: 14/610,185

(22) Filed: Jan. 30, 2015

(65) Prior Publication Data
US 2015/0209549 A1 Jul. 30, 2015

(30) Foreign Application Priority Data

Jan. 30, 2014 (GB) .................................... 1401552.3
Jul. 22, 2014 (GB) .................................... 1412941.5

(51) Int. Cl.
*A61M 25/00* (2006.01)

(52) U.S. Cl.
CPC ................................ *A61M 25/0067* (2013.01)

(58) Field of Classification Search
CPC ......... A61M 2210/0693; A61B 5/6864; A61B 5/6868
See application file for complete search history.

(56) References Cited

U.S. PATENT DOCUMENTS

| | | | |
|---|---|---|---|
| 5,935,795 A | 8/1999 | Lin et al. | |
| 6,042,579 A | 3/2000 | Elsberry et al. | |
| 6,348,050 B1 | 2/2002 | Hartlaub | |
| 6,609,020 B2 | 8/2003 | Gill | |
| 7,974,696 B1 | 7/2011 | DiLorenzo | |
| 2003/0203844 A1 | 10/2003 | Delfani et al. | |
| 2007/0161919 A1* | 7/2007 | DiLorenzo ......... | A61B 5/04001 600/544 |
| 2009/0011980 A1* | 1/2009 | Gill ..................... | A61K 38/185 514/1.1 |

(Continued)

FOREIGN PATENT DOCUMENTS

| | | |
|---|---|---|
| WO | 03/077785 A1 | 9/2003 |
| WO | 2008/062173 A1 | 5/2008 |

(Continued)

OTHER PUBLICATIONS

Anderson et al., "Convection enhanced delivery of topotecan into diffuse intrinsic brainstem tumors in children", J Neurosurg Pediatrics 11, pp. 289-295, 2013.

(Continued)

*Primary Examiner* — Deanna K Hall
(74) *Attorney, Agent, or Firm* — Oliff PLC

(57) ABSTRACT

A method for delivering fluid to the brain of a subject using an intraparenchymal catheter, the method comprising the step of inserting the catheter into the brain using a posterior to anterior approach and methods of treating neurodegenerative disorders using this delivery method, as well as methods for delivering fluid to an elongate structure of the brain using an intraparenchymal catheter, the method comprising the step of inserting a catheter into the brain along an insertion axis that is substantially aligned with a long axis of the elongate structure.

15 Claims, 19 Drawing Sheets

(56) References Cited

U.S. PATENT DOCUMENTS

2009/0222067 A1    9/2009    Toselli et al.
2017/0143966 A1    5/2017    Reymers et al.

FOREIGN PATENT DOCUMENTS

WO    2008/098769 A1    8/2008
WO    2014/016591 A1    1/2014

OTHER PUBLICATIONS

Barua et al., "Robot-guided convection-enhanced delivery of carboplatin for advanced brainstem glioma", Acta Neurochir, 7 pages, 2013.

Brady et al., "Pathways of Infusate Loss During Convection Enhanced Delivery into the Putamen Nucleus", Stereotact Funct Neurosurg. 20134 91(2), pp. 69-78, 2013.

Chen et al., "Variables affecting convection-enhanced delivery to the striatum; a systematic examination of rate of infusion, cannula size, infusate concentration, and tissue-cannula sealing time", J Neurosurg 90, pp. 315-320, 1999.

Freed et al., "Transplantation of embryonic dopamine neurons for severe Parkinson's disease", The New England Journal of Medicine, vol. 344, No. 10, pp. 710-719, 2001.

Gill et al., "Direct brain infusion of glial cell line-derived neurotrophic factor in Parkinson disease", Nature Medicine, pp. 1-7, 2003.

Rosenblad et al., "Sequential Administration of GDNF into the Substantia Nigra and Striatum Promotes Dopamine Neuron Survival and Axonal Sprouting but Not Striatal Reinnervation or Functional Recovery in the Partial 6-OHDA Lesion Model", Experimental Neurology, 161, pp. 503-516, 1999.

Slevin et al., "Improvement of bilateral motor functions in patients with Parkinson disease through the unilateral intraputaminal infusion of glial cell line-derived neurotrophic factor", J Neurosurg, 102, pp. 216-222, 2005.

Murata et al., "Electrical stimulation of the posterior subthalamic area for the treatment of intractable proximal tremor", J. Neurosurg., vol. 99, Oct. 2003, pp. 708-715.

Sep. 29, 2017 Office Action issued in U.S. Appl. No. 15/095,722.

Bejjani et al., "Bilateral subthalamic for Parkinson disease by using three-dimenional sterotactic magnetic reasonance imaging and electrophysiological guidanc", J Neurosurg 92:615-625, Apr. 2000.

May 22, 2018 Notice of Allowance issued in U.S. Appl. No. 15/095,722.

U.S. Appl. No. 15/095,722, filed Apr. 11, 2016 in the name of Gill.

\* cited by examiner

NEUROSURGICAL APPARATUS AND METHOD

TECHNICAL FIELD

This application is directed to an improved neurosurgical apparatus and method.

BACKGROUND

Relatively large lenticulo striate arteries penetrate the most ventral portion of the putamen and course through it from ventral to dorsal to supply the basal ganglia and internal capsule. In passing through the putamen the calibre of the vessels reduces from ventral to dorsal and so do the perivascular spaces. The perivascular spaces are in direct communication with the extra cellular fluid in the putamen and arterial pulsations in the lenticulo striate vessels act in cooperation with the peri-vascular spaces to create fluid pumps that drive extra cellular fluid dorsoventrally in the opposite direction to the arterial supply. The extra cellular fluid is cleared into the perivascular spaces with increasing efficiency as one moves from the dorsal to the ventral putamen as a consequence of the increasing calibre of the lenticulo striate vessels.

When delivering a drug by convection enhanced delivery into the putamen or other regions of the brain to treat conditions such as Parkinson's disease, Huntington's disease or other neurodegenerative disease, it is desirable to fill the greater proportion of the target area with the infused drug. It has been observed that poor volumetric distribution of drug infused, for example, into the putamen down a fine catheter when the tip of the catheter is in close proximity to large calibre lenticulo striate vessels in the ventral portion of the putamen. This is due to a higher rate of clearance of extra cellular fluid and thus drug in the ventral portion of the putamen than there is in its dorsal portion as a consequence of the large calibre perivascular pumps.

Catheters or cannulae have previously been passed into regions of the brain, such as the putamen, for the delivery of drugs (or transplanted cells) through a frontal burr hole at an angle of approximately 45° to the anterior commissure-posterior commissure plane. The disadvantage of this trajectory is that, in order to place an adequate length of the catheter or cannula within the putamen the frontal entry point in the skull needs to be very close to the mid sagittal plane because of the orientation of the putamen which angles laterally from its anterior to posterior aspect. The putamen also angles from medial to lateral in the vertical or coronal plane from its dorsal to ventral aspect. A frontal entry point close to the mid sagittal plane increases the risk of causing haemorrhage because the calibre and density of the veins draining the cortex into the sagittal sinus increase as they approach the midline. The putamen is bean shaped with a concavity on its medial aspect and is tapered at its posterior end. A trajectory entering its most dorsal portion and passing at 45° into it will result in a relatively short catheter length contained within the putamen if the distal end of the catheter is to remain within the structure. The short length of catheter that is within the structure limits the volume of drug that can be infused into the putamen as there is a tendency for the drug to reflux along the length of the catheter, generally giving an elongate infusion volume. As described above, the clearance of extracellular fluid and therefore of the infused drug will be greatest in the most ventral portion of putamen where the enlarged perivascular spaces act as fluid sumps. This will limit the distribution of the drug into the more dorsal aspects of the structure. An additional disadvantage of the above described trajectory is that the distal end of the catheter will be passing into a portion of the putamen which is densely supplied by large calibre lenticulo striate vessels and therefore the risk of haemorrhage is increased.

Particular problems associated with delivering infusate to the putamen of rhesus and cynomolgous monkeys were described in Brady et al. 2013, which measured the loss of volume due to overflow, perivascular flow, backflow and catheter tract leakage. Brady carried out infusions using catheters inserted from a superior position, which is the commonly accepted approach to target structures in the brain (as described in Slevin et al. 2005). However, Brady notes that an axial catheter trajectory passing through the frontal sinuses, although not commonly used due to technical difficulties in implanting catheters through this structure and the risk of infection when traversing the mucosa lined sinus, may have a geometric advantage due to the catheter being inserted along the long axis of the putamen.

In view of the problems associated with delivering fluid to the brain there is a need to provide improved methods for this delivery.

SUMMARY

In a first embodiment, there is provided a method for delivering a fluid to a brain of a subject. The method may include delivering the fluid to the brain by inserting at least one intraparenchymal catheter into a target area of the brain using a posterior to anterior approach.

In another embodiment, there is provided a method for treating a neurodegenerative disorder. The method may include delivering a fluid to a brain of a subject by inserting at least one intraparenchymal catheter into a target area of the brain using a posterior to anterior approach.

In another embodiment, there is provided a method for delivering a fluid to an elongate structure of a brain of a subject. The method may include delivering the fluid to the elongate structure by inserting at least one intraparenchymal catheter into the brain along an insertion axis that is substantially aligned with a long axis of the elongate structure.

BRIEF DESCRIPTION OF TH DRAWINGS

FIGS. 1 to 3 illustrate prior techniques that involve inserting catheters through a frontal burr hole at an angle of approximately 45° to the anterior commissure-posterior commissure plane.

FIGS. 4 to 6 shows catheter placement in accordance with an embodiment. The catheter can thus be seen to extend substantially along the long axis of the putamen. Fluid thus refluxes back from the catheter tip to the step in the outer surface profile of the catheter, thereby providing a distribution that covers a large part of the putamen.

DETAILED DESCRIPTION

Figure 18:
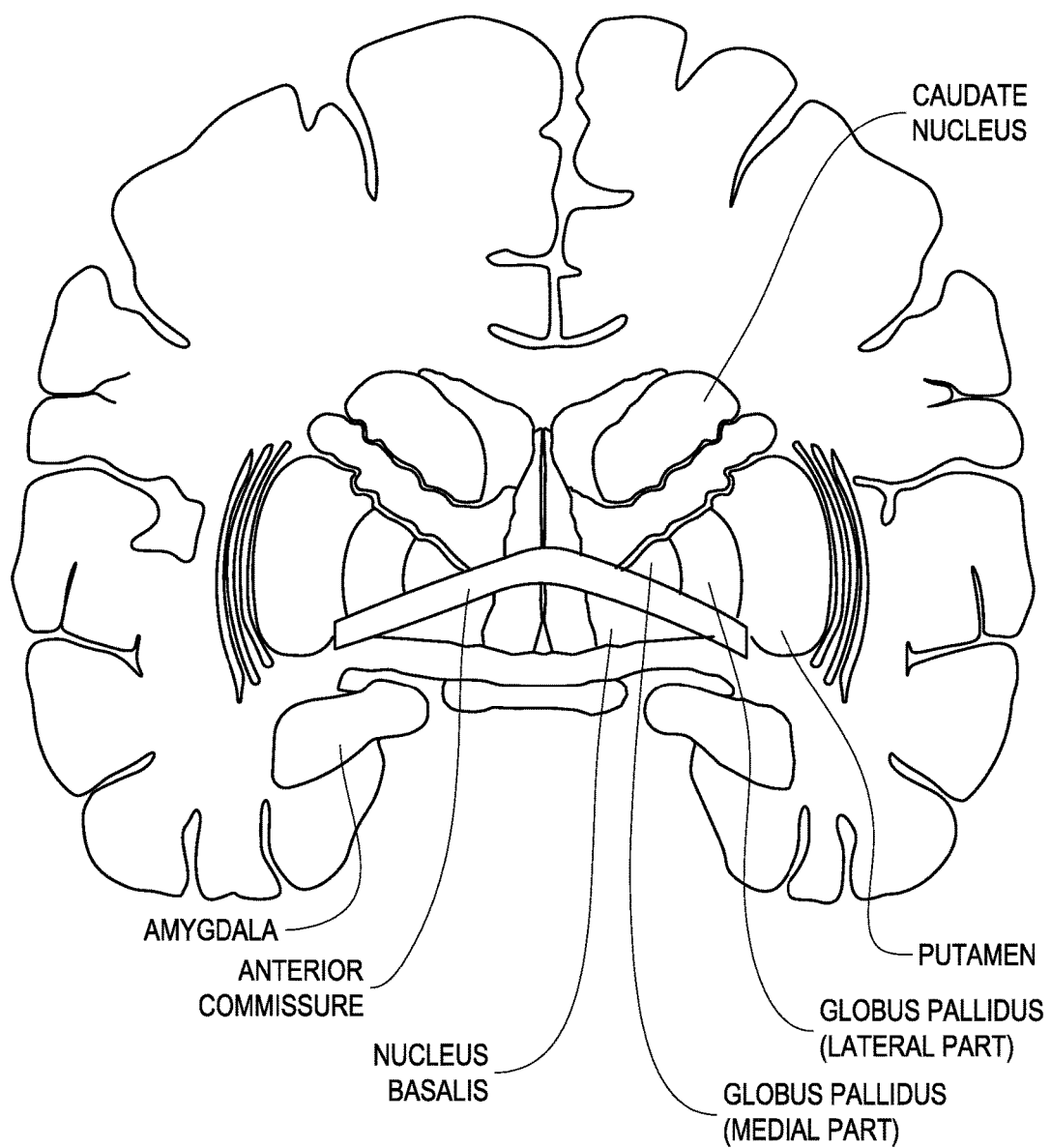
FIG. 18 shows a schematic coronal view of the human brain.
Figure 19:
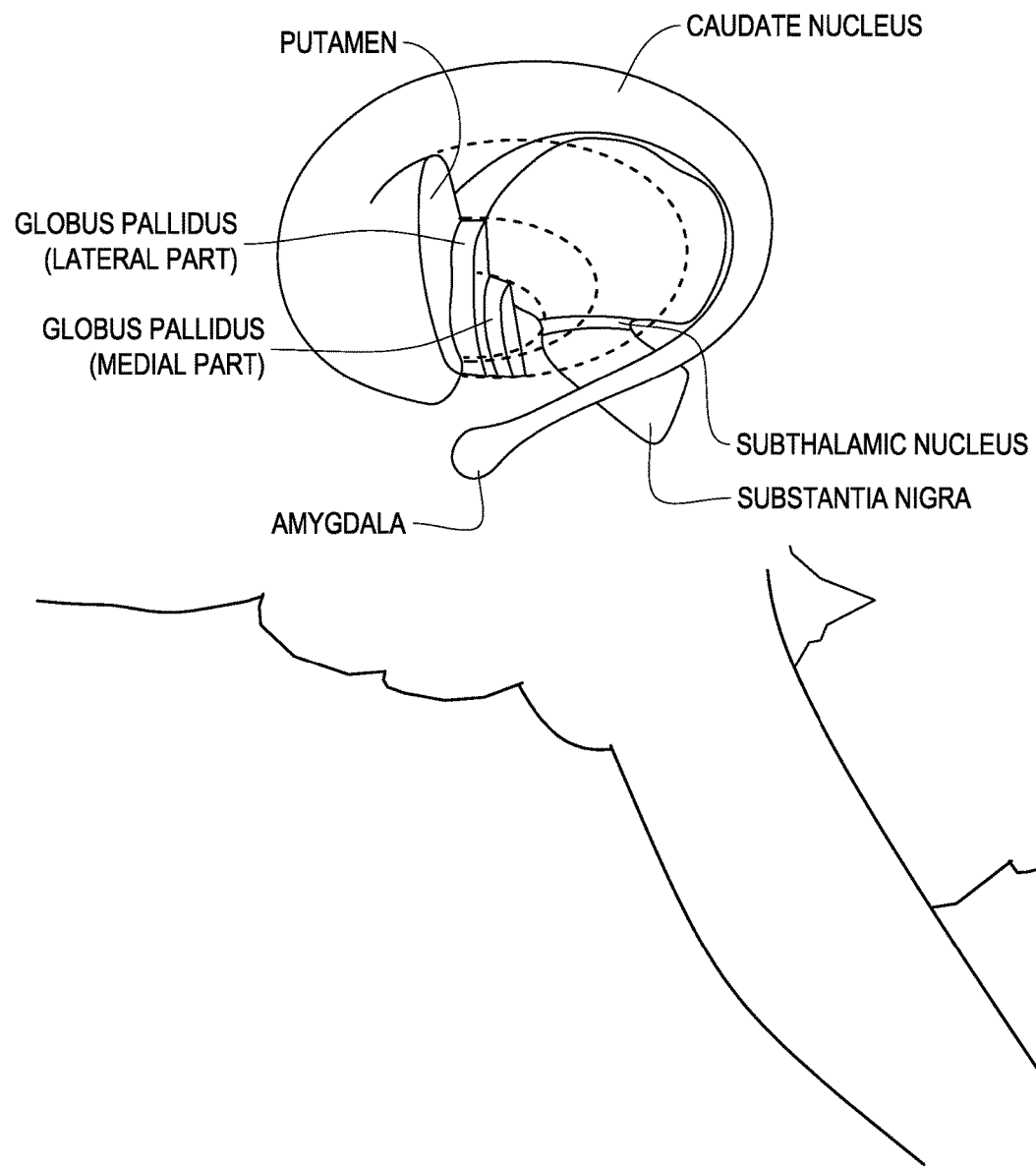
FIG. 19 shows a schematic perspective view of the basal ganglia of the human brain.
Figure 20:
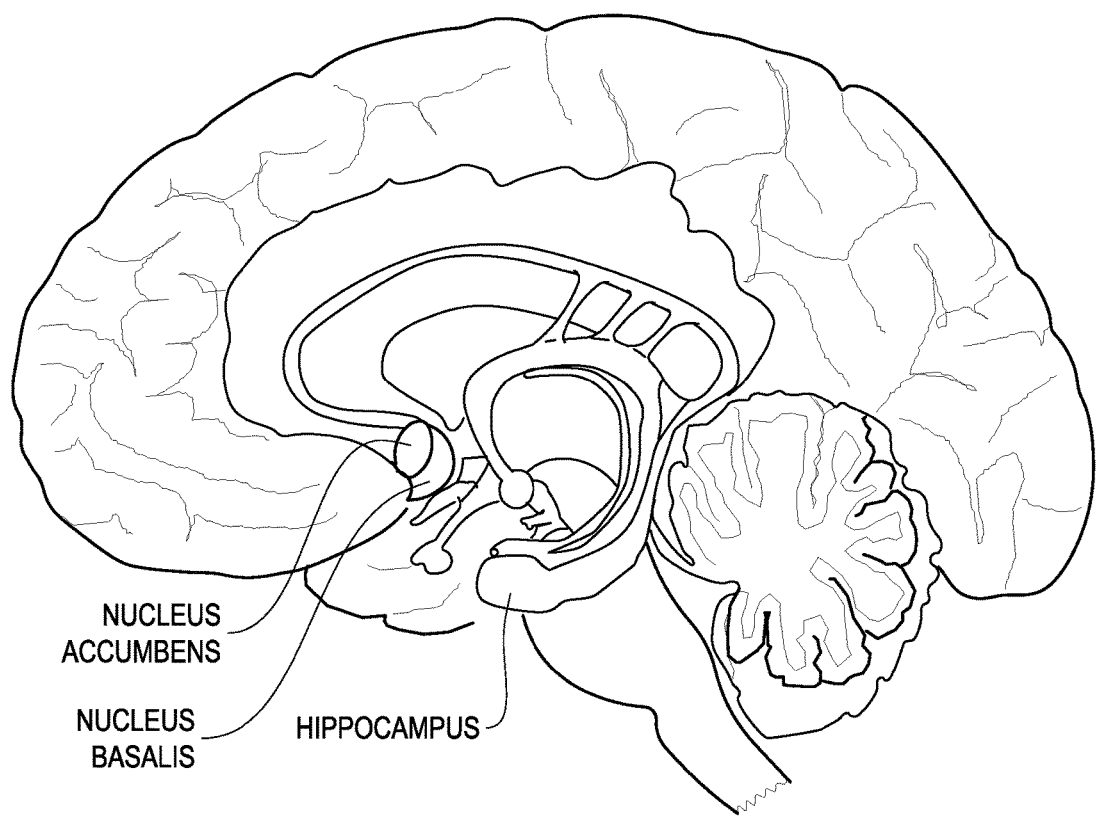
FIG. 20 shows another schematic sagittal view of the human brain.

In disclosed embodiments, the fluid may be delivered to structures within the brain, including one or more of the hippocampus, the putamen, the globus pallidus, the amygdala, the nucleus basalis, the nucleus accumbens, the substantia nigra, the caudate nucleus and the subthalamic nucleus, as shown in FIGS. 18, 19 and 20. The target structures preferably have a long axis orientated in an anterior to posterior direction. This particular orientation allows the structures to be targeted along their length, allowing a greater length of catheter to be inserted into the structure, which can reduce catheter reflux. Accordingly, more fluid can be delivered into the structure.

Figure 17:
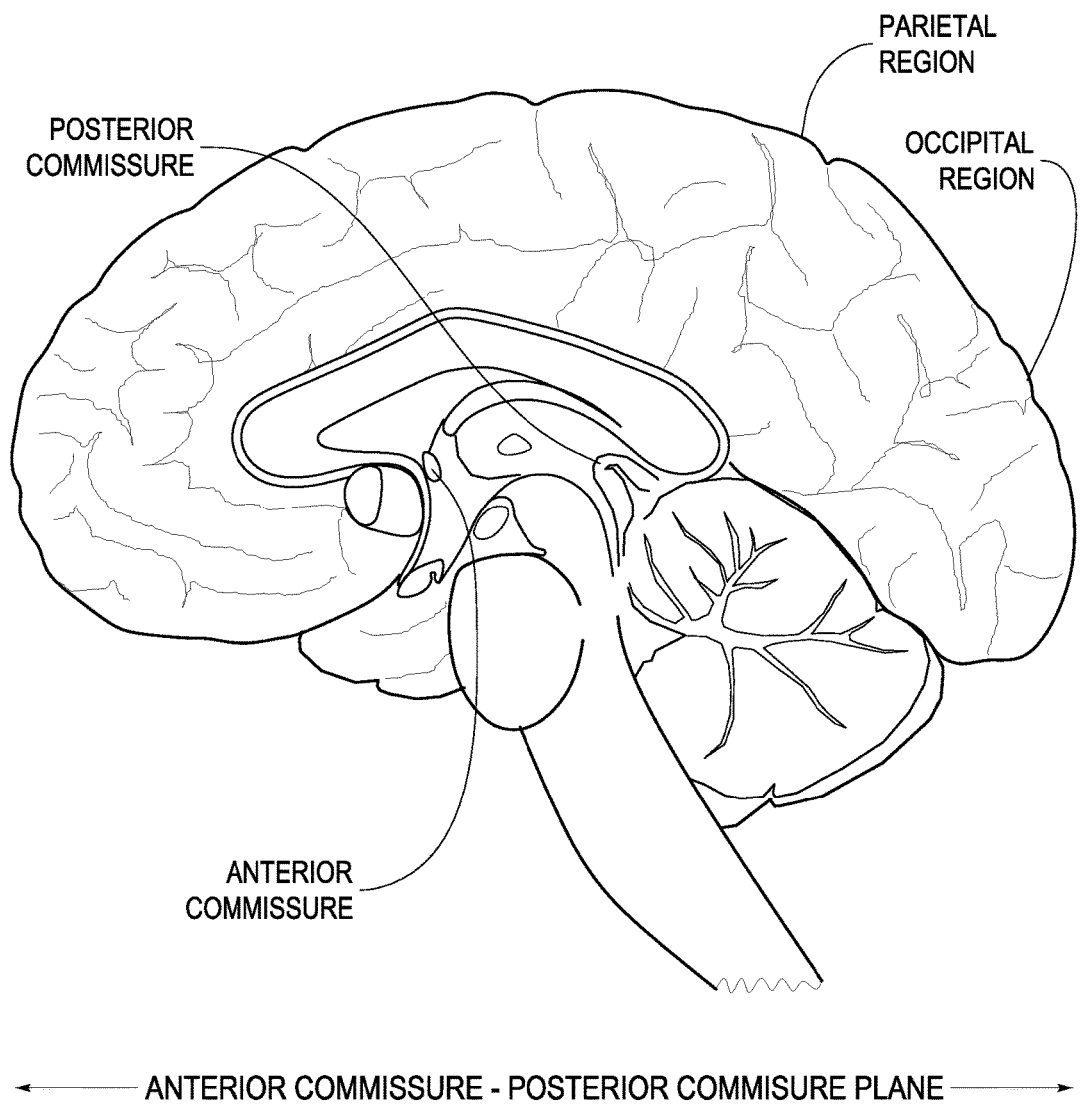
FIG. 17 shows a schematic sagittal view of the human brain.

In a preferred embodiment, the catheter is inserted along a trajectory through the occipitoparietal region, approximately parallel to the anterior commissure-posterior commissure plane, as shown in FIG. 17.

The posterior to anterior approach allows the disclosed method to be carried out on a subject such as a patient under general anaesthetic and in a prone position. Movement of the brain during neurosurgery can be a particular problem as even a few millimeters of displacement can significantly affect the accuracy of e.g. a catheter inserted into the brain. Not only will the brain move if and when the patient is moved, but the action of inserting a catheter can itself displace the brain in the direction of the insertion. Indeed, the present inventors have identified that during a conventional superior/vertical approach into the brain the brain can displace in potentially two different directions, making it difficult for surgeons to finely control catheter placement. However, the prone position of the patient in disclosed methods can have advantages, as when the patient is turned from their back onto their front the brain displaces anteriorly in the skull. The catheter insertion is then from the posterior toward the anterior, however, as the brain has already displaced anteriorly any further displacement due to catheter insertion is likely to be minimal. The disclosed methods can therefore provide highly accurate targeting of structures in the brain. In preferred embodiments, the patient may be a human.

The insertion trajectory may be substantially aligned with the long axis of a target structure, such as the hippocampus, the putamen, the globus pallidus, the amygdala, the nucleus basalis, the nucleus accumbens, the substantia nigra, the caudate nucleus and the subthalamic nucleus. In order to improve the distribution of an infused drug delivered by CED into a target structure, in embodiments, the method comprises using a catheter insertion trajectory that passes from posterior to anterior through the occipital, occipitoparietal, or occipitotemporal region approximately parallel to the anterior commissure-posterior commissure plane. When targeting the long axis of the putamen (which may include the head of the caudate nucleus along the same trajectory), the globus pallidus, the nucleus basalis, the nucleus accumbens, the amygdala, the substantia nigra, the subthalamic nucleus, or the hippocampus, this trajectory preferably passes through the optic radiation, lateral to the posterior horn of the lateral ventricle and thence into the posterior part of the structure and along its long axis to its anterior portion.

The fluid may be delivered into structures of the brain that are at least 2 cm or at least 4 cm or at least 6 cm from the skull of the patient. The structures may be in areas of the forebrain and/or in areas of the midbrain.

In another embodiment, the method may include delivering a fluid (e.g. a fluid containing a therapeutic agent) to the brain. The fluid delivery is conveniently by convection enhanced delivery (CED). The method preferably comprises the step of inserting a catheter into the brain along a trajectory through the occipitoparietal region approximately parallel (e.g. parallel to within 10°, 20°, 30°, or 40°) to the anterior commissure-posterior commissure plane. The trajectory preferably passes from posterior to anterior.

In another embodiment, the method may include delivering a fluid to a target structure such as the hippocampus, the putamen, the globus pallidus, the amygdala, the nucleus basalis, the nucleus accumbens, the substantia nigra, the caudate nucleus and the subthalamic nucleus that comprises the step of inserting a catheter into the brain along an axis that is substantially aligned (e.g. to within 10°, 20°, 30° or 40°) with the long axis of the structure. The insertion trajectory preferably passes from posterior to anterior.

An advantage of disclosed embodiments is that the inserted catheter will have a greater portion confined to the target structure, typically about 10 to about 40 mm or about 15 to about 30 mm, whereas a more vertical trajectory through the frontal region could achieve a catheter length of between 10 and 15 mm most typically. Indeed, the upper limit for the length of the catheter confined to the target structure using methods of disclosed embodiments is limited only by the size of the target structure in the patient.

Importantly, the catheter placed along the long axis of the putamen would avoid the larger calibre and greater density of lenticulo striate vessels, reducing the likelihood of causing haemorrhage and reducing the impact of perivascular pumping of fluid from the extracellular space which is greater as one moves from the dorsal to the ventral striatum. This also has the advantage of potentially increasing the volume of distribution in the target structure and as drug would be drawn ventrally by the flow of extracellular fluid which occurs predominantly in a dorsoventral direction, this would achieve greater total coverage of the structure than would be achieved by the more conventional trajectory. Passing the catheter tip along this trajectory into the head of the caudate nucleus would be advantageous for treating Huntingdon's, multiple system atrophy and cortico-basal degeneration.

Optimising the volume of distribution of therapy within regions of the brain, such as the hippocampus, the putamen, the globus pallidus, the amygdala, the nucleus basalis, the nucleus accumbens, the substantia nigra, the caudate nucleus and the subthalamic nucleus, and avoiding inadvertent clearance along the perivascular spaces is particularly important when delivering viral vectors for gene therapy. This is because uncontrolled transfection of neurons at distant sites within the CNS could cause long-term and debilitating side effects.

The method may be used to deliver any therapeutic agent. The method may be used to treat conditions such as Parkinson's disease, Huntington's disease, Alzheimer's disease, Multiple-System Atrophy, Progressive Supranuclear Palsy (PSP), dystonia, tremor, Tourette's syndrome or other neurodegenerative diseases.

The therapeutic agent may be selected from, for example, one or more of a chemotherapy drug, a neurotrophin, an enzyme, a growth factor, an antibody, an immunotoxin, small inhibitory RNA (siRNA), antisense oligonucleotides, viral vectors, drug releasing nanoparticles (including liposomes and micels), transgenes and combinations or mixtures thereof. In embodiments, the therapeutic agent may be glial cell-derived neurotrophic factor (GDNF) or neprilysin, which may be adminsitered alone or in combination or consecutively. The combination and/or consecutive administration of GDNF and neprilysin may be used for the treatment of Alzheimer's disease.

The therapeutic agent may be administered in combination with artificial cerebrospinal fluid (aCSF). ACSF as disclosed herein may comprise glucose, proteins and ionic constituents. Alternatively, the aCSF may omit glucose, so as to reduce the likelihood of bacterial growth in any catheter used to administer the composition to a subject. Most preferably, the aCSF does not comprise glucose or proteins.

In another embodiment, the method may include treating a neurodegenerative disorder, the method comprising delivering fluid to the brain of a patient using an intraparenchymal catheter, wherein the catheter is inserted into the brain using a posterior to anterior approach as described above.

In a further aspect, the method may include delivering fluid to an elongate structure of the brain using an intraparenchymal catheter, the method comprising the step of inserting a catheter into the brain along an insertion axis that is substantially aligned with a long axis of the elongate structure. Suitable elongate structures include the hippocampus, the putamen, the globus pallidus, the amygdala, the nucleus basalis, the nucleus accumbens, the substantia nigra, the caudate nucleus or the subthalamic nucleus.

Disclosed embodiments may use a catheter of the type described in WO03/077785 (incorporated herein by reference) that is inserted via a guide tube. A recessed step catheter as described in WO2014/016591 (incorporated herein by reference) may also be used. Advantageously, a catheter and/or cannula having a stepped outer profile may be employed.

Any step or steps in the outer profile are preferably located within the structure of the putamen. In addition to the surgical methods outlined above, embodiments extend to a catheter adapted for insertion in accordance with the method described above. The method may involve implanting a percutaneous port based catheter system, for example as described in WO2008/062173 or WO2011/098769 (both incorporated herein by reference).

The fluid may be administered via at least one convection enhanced delivery (CED) catheter, especially an intraparenchymal catheter. Alternatively, the fluid may be administered via at least two, at least three or four or more such catheters. For example, two catheters may be used to administer the fluid bilaterally.

The fluid may be delivered via at least one or at least two chronically implanted CED catheters or via three or more of such catheters. Chronically implanted CED catheters refer to catheters that will be left in situ in the brain of a subject for at least 30 days, optionally for at least six months. Chronically implanted catheters may remain in place for up to one year or even for the lifetime of a subject.

The fluid may be administered on at least two, preferably three, optionally four consecutive days. Alternatively, the fluid may be administered on two out of three, four or five days, or three out of four, five, six or seven days.

Whether or not the fluid is for administration for a number of consecutive days or for regular administration over a number of days, it may independently or additionally be for administration weekly, fortnightly, monthly, every six, eight, twelve or fifteen or more weeks. For example, a cycle of two or three days of infusions may be repeated every fortnight. Alternatively, it may be for administration in a series of cycles of infusions, with 6, 7, 8, 9, 10, 11 or 12 days between the end of a first cycle of infusions and the next cycle of infusions.

For example, the fluid may be for administration by infusion for between 6 and 10, especially between 7 and 9 hours, each day for three consecutive days. This pattern of administration may then be repeated weekly, or fortnightly, or for example with 6, 7, 8, 9, 10, 11 or 12 days between the end of a first cycle of three days of infusions and the next three days of infusions.

Examples

Artificial cerebrospinal fluid with an MRI visible tracer (Gadolinium) was infused into the human putamen through intra-cerebrally placed neuro catheters as described in WO 2014/016591. The surgery utilised a robot-guided stereotactic CED system as described in Barua et at 2013 to compare the volume of distribution following (i) a conventional vertical approach into the putamen with (ii) an anterior to posterior insertion trajectory and (iii) a posterior to anterior insertion trajectory.

Both the anterior to posterior and posterior to anterior trajectories passed approximately parallel to the anterior commissure-posterior commissure plane to target the long axis of the putamen. The entry point for the anterior to posterior trajectory was located between the orbits and the coronal suture, while the posterior to anterior trajectory had an entry point in the occipitoparietal region and passed through the optic radiation, lateral to the posterior horn of the lateral ventricle.

Quantification of the infusion distribution was made possible through the use of Renishaw's NeuroInspire™ (Renishaw Plc., Gloucestershire, UK) surgical planning software with an in-house software module. Clinical guidance was given to define the boundaries of the infusions and profiles were manually drawn around the visible infusion on each MRI slice. The software module then reconstructs the profiles into a 3D volume, multiplying the areas by the slice thickness.

Figure 1:
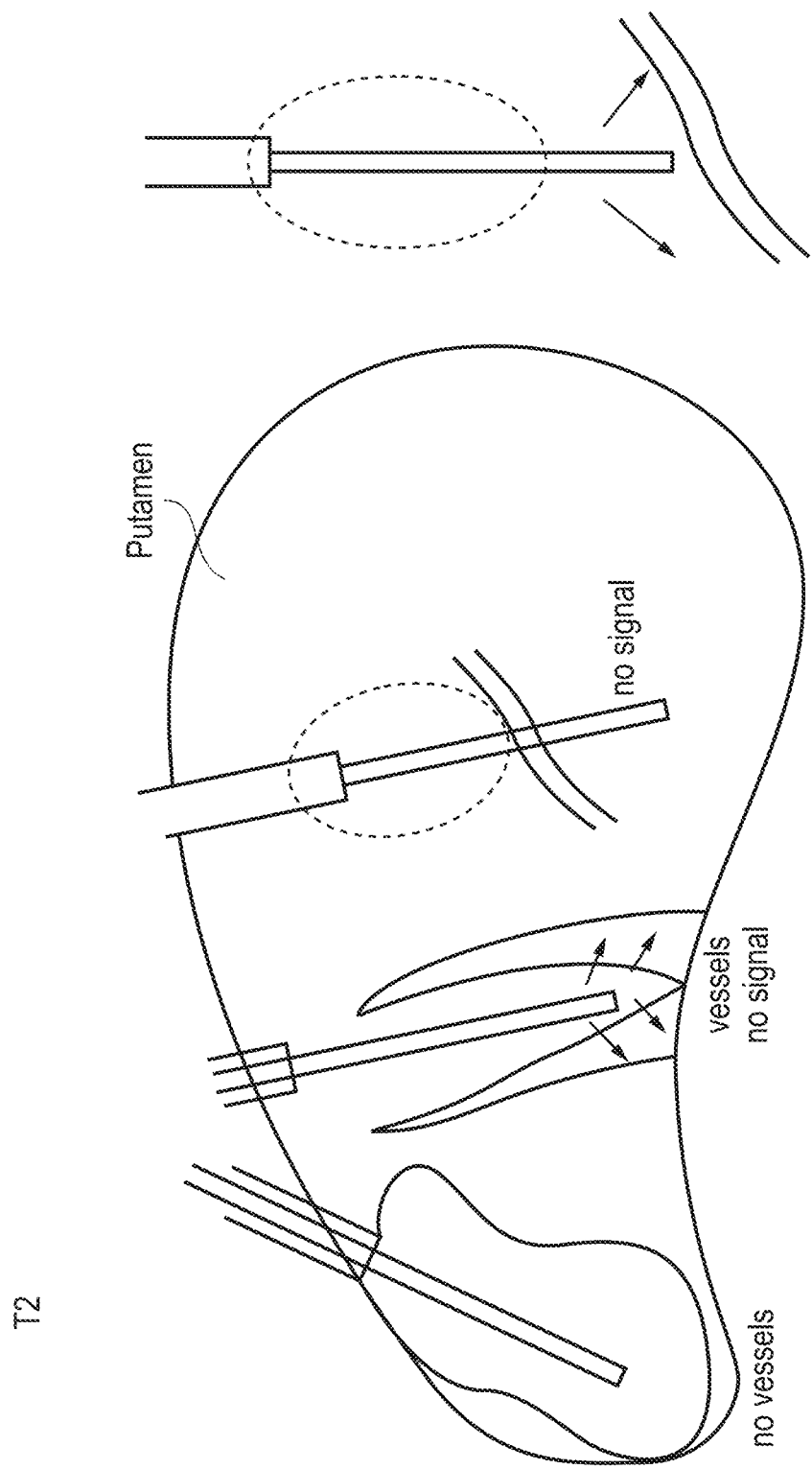
Figure 2:
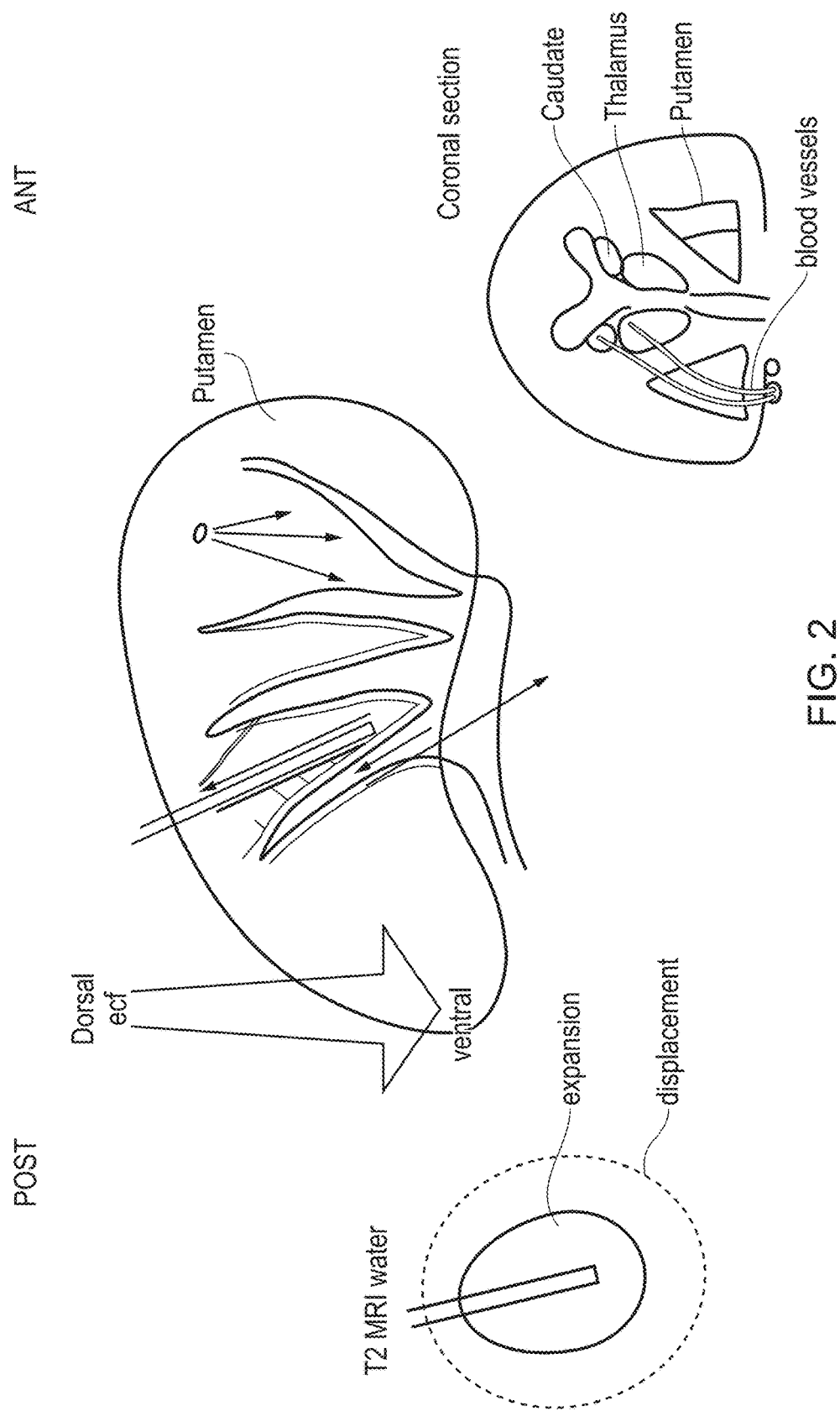
Figure 3:
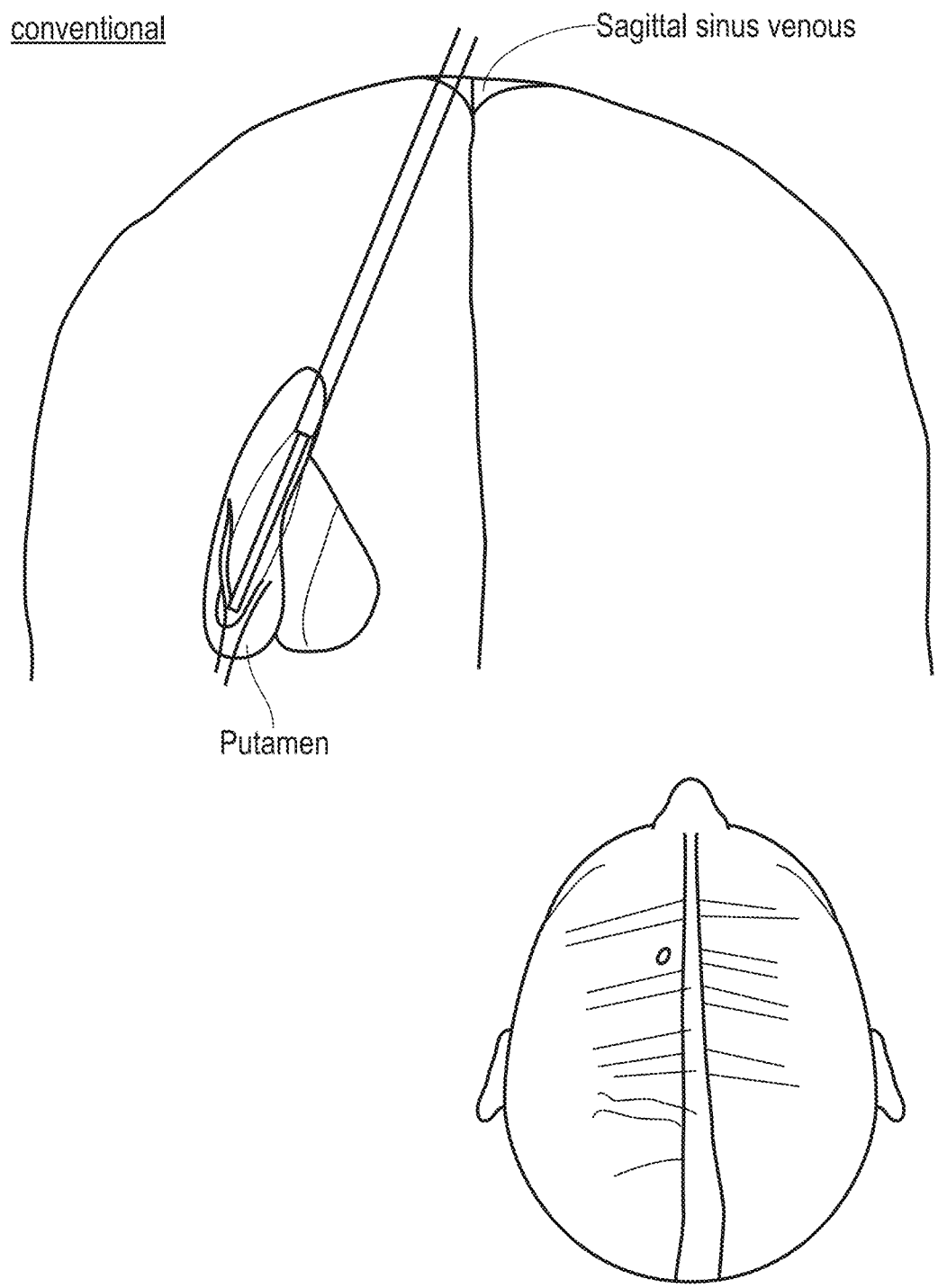
Figure 4:
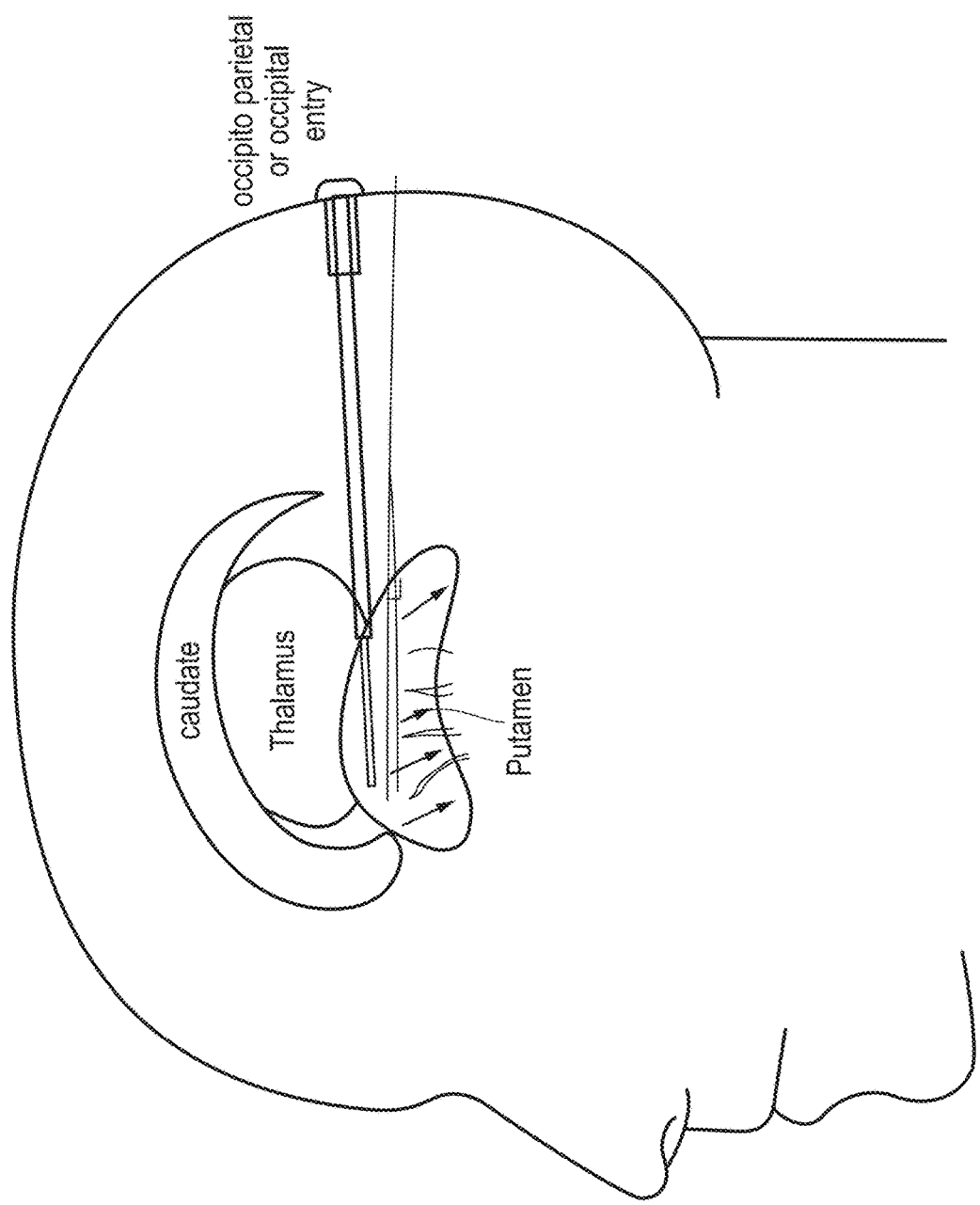
Figure 5:
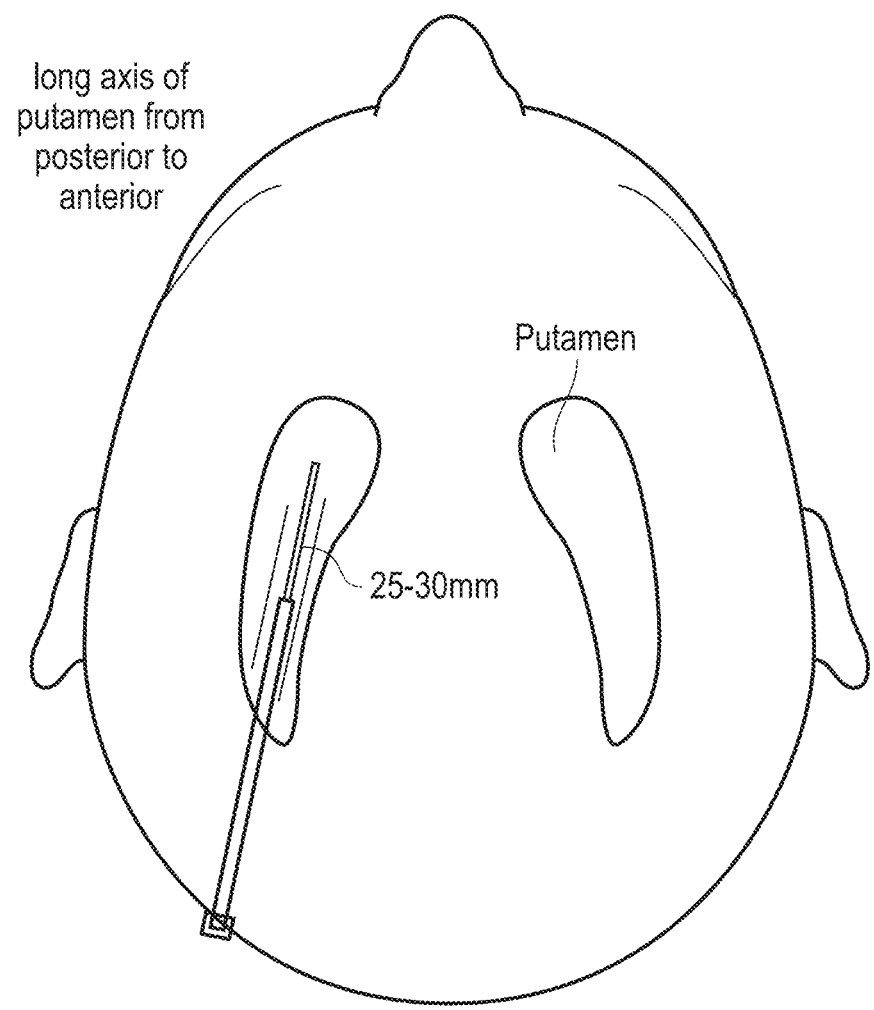
Figure 6:
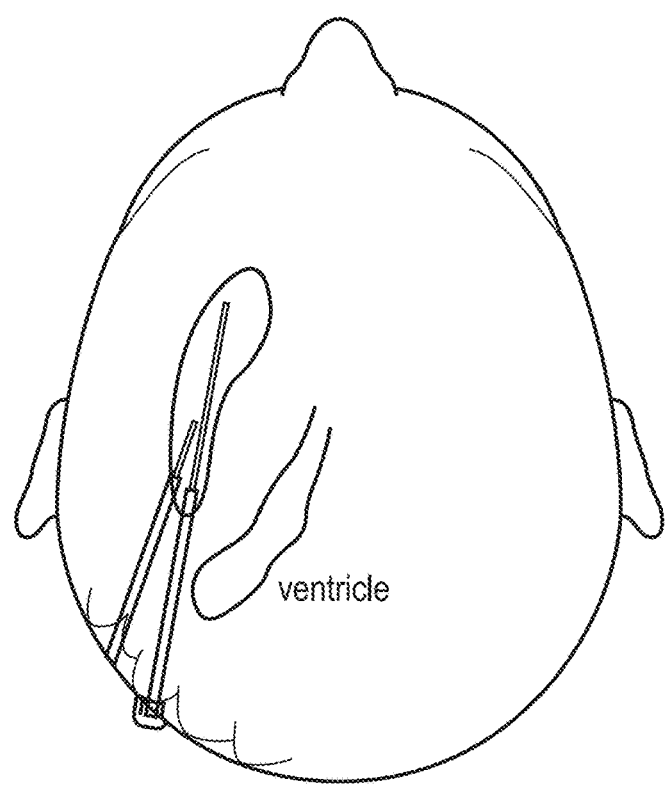
Figure 7:
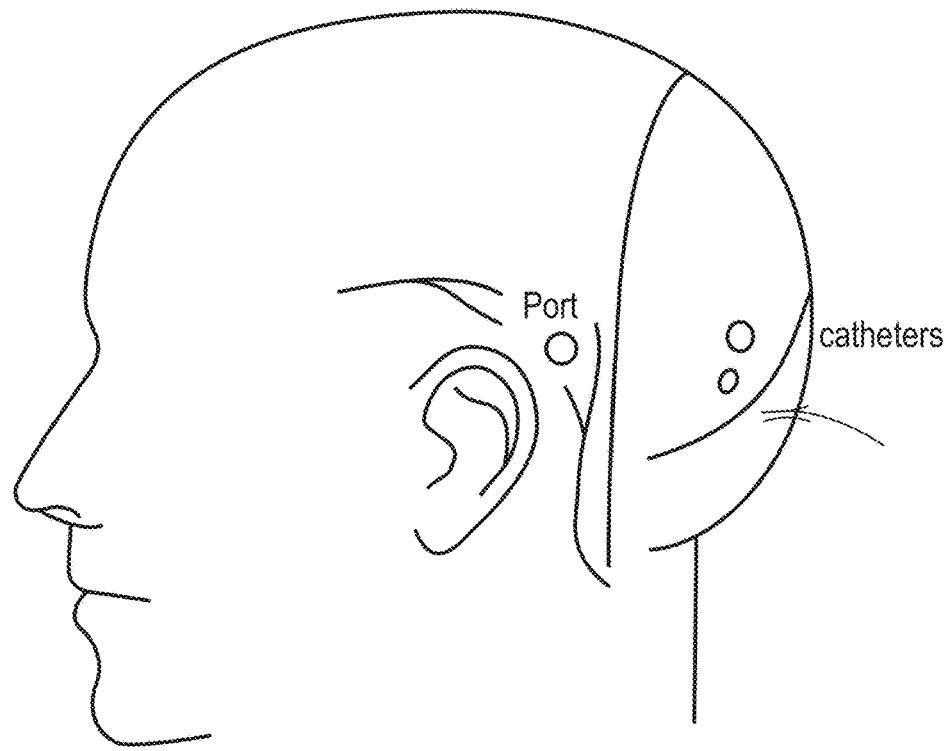
FIG. 7 shows how a percutaneous port based system may be used to provide a fluid connection to catheters placed in accordance an embodiment.
Figure 8:
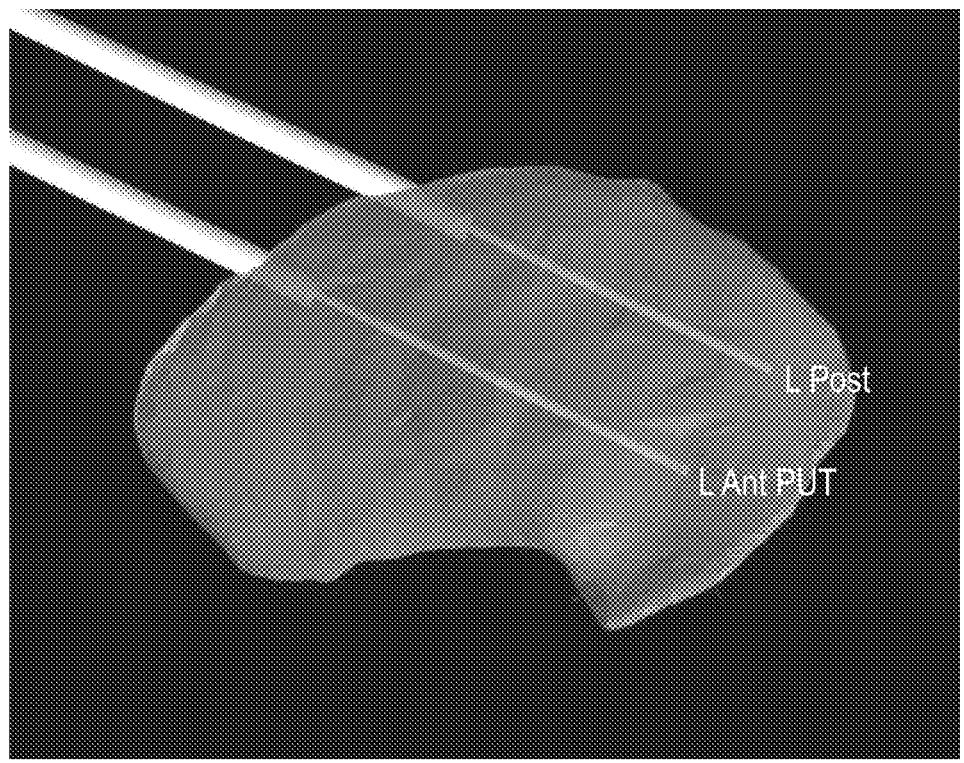
FIGS. 8 and 9 show an anterior to posterior trajectory for catheter delivery to the putamen and FIGS. 10 to 13 illustrate delivery achieved using an anterior to posterior trajectory.
Figure 9:
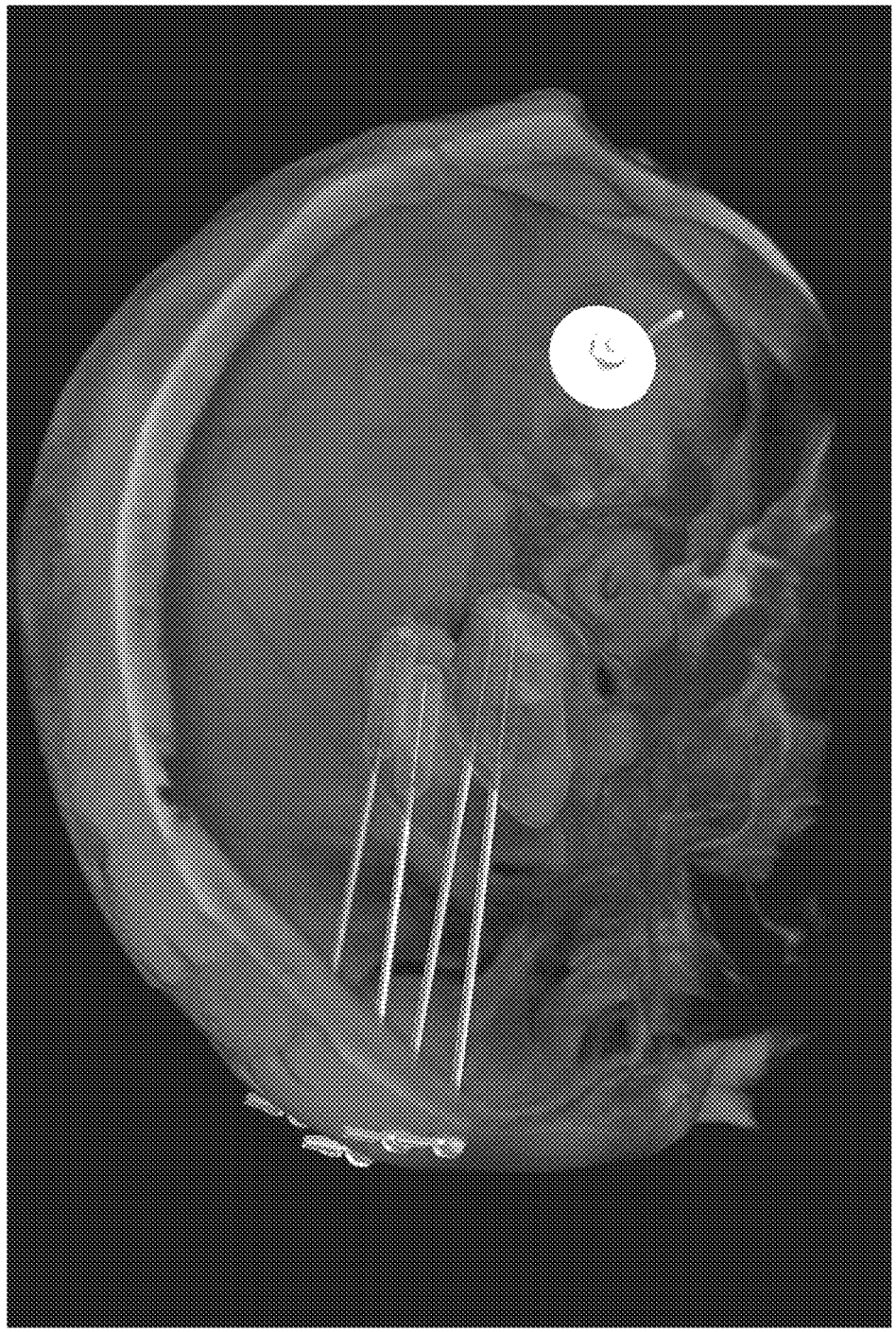
Figure 10:
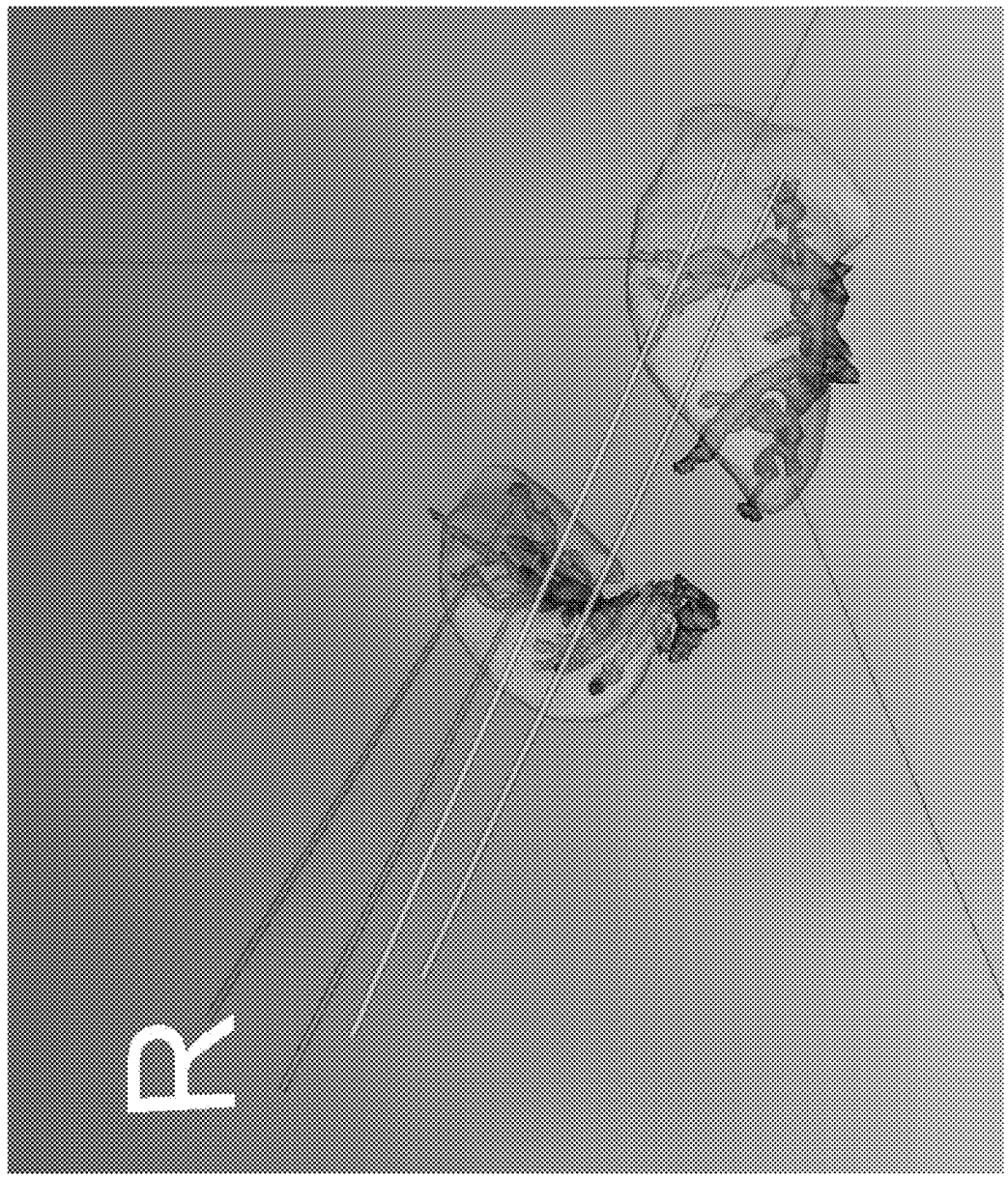
Figure 11:
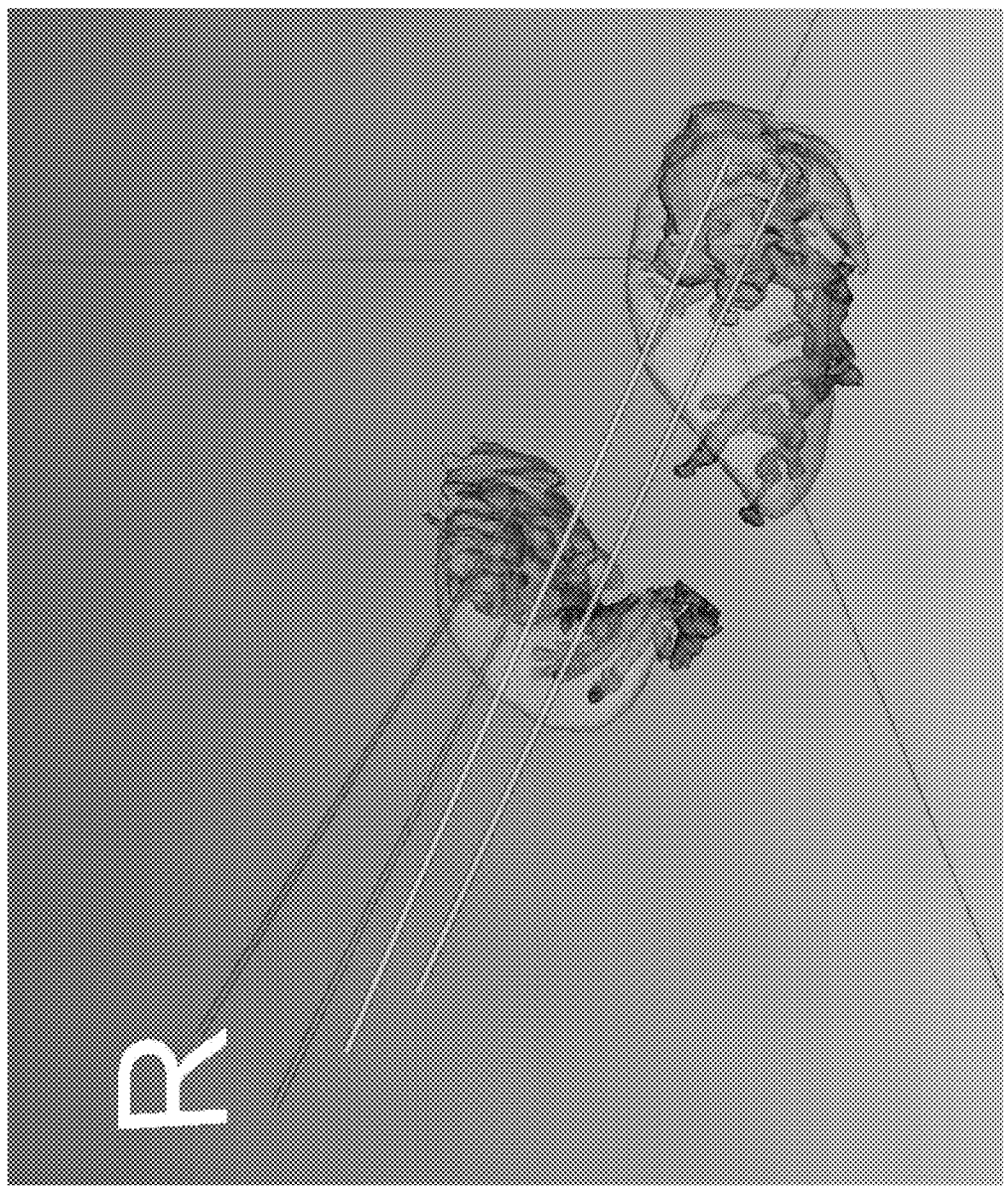
Figure 12:
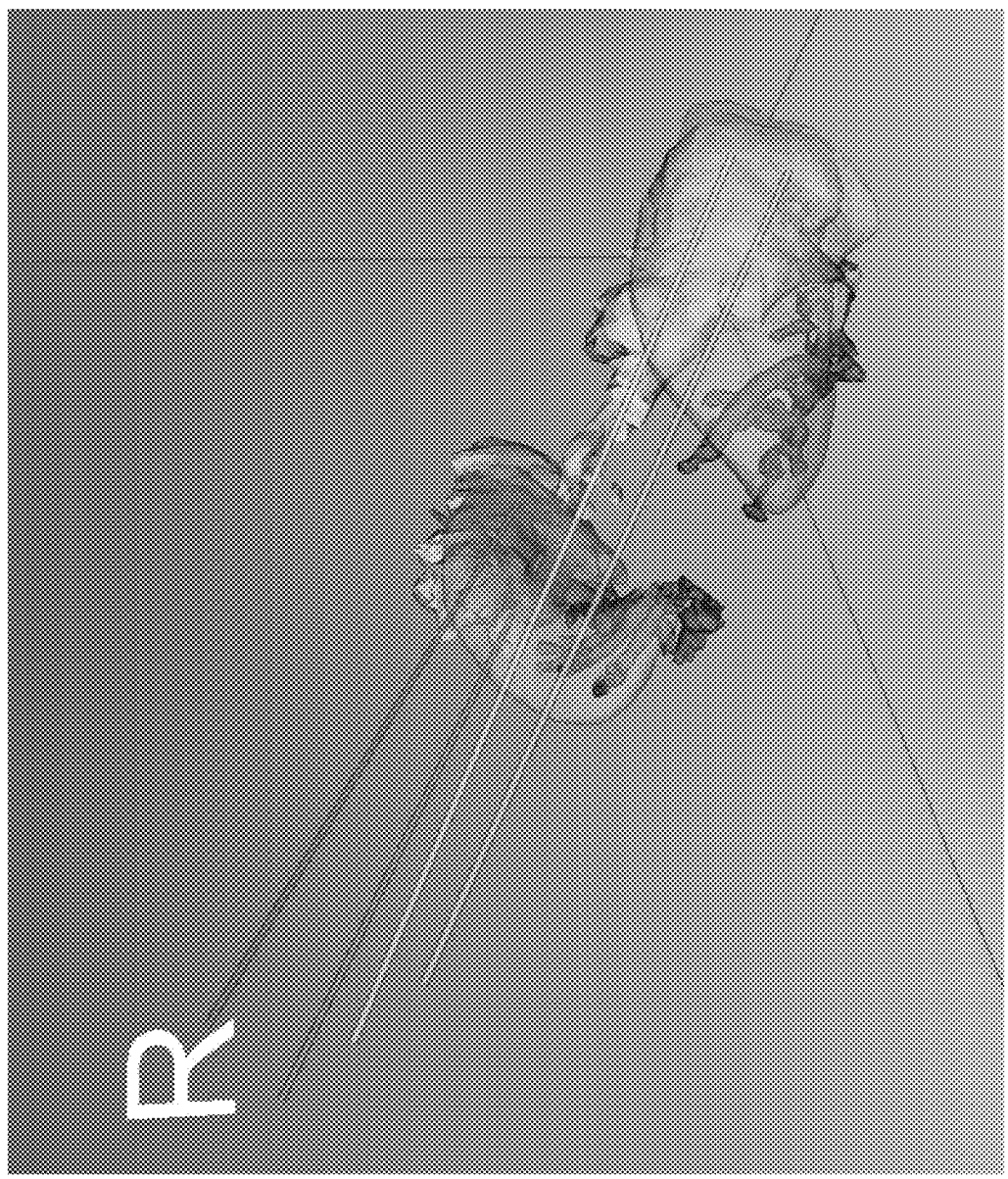
Figure 13:
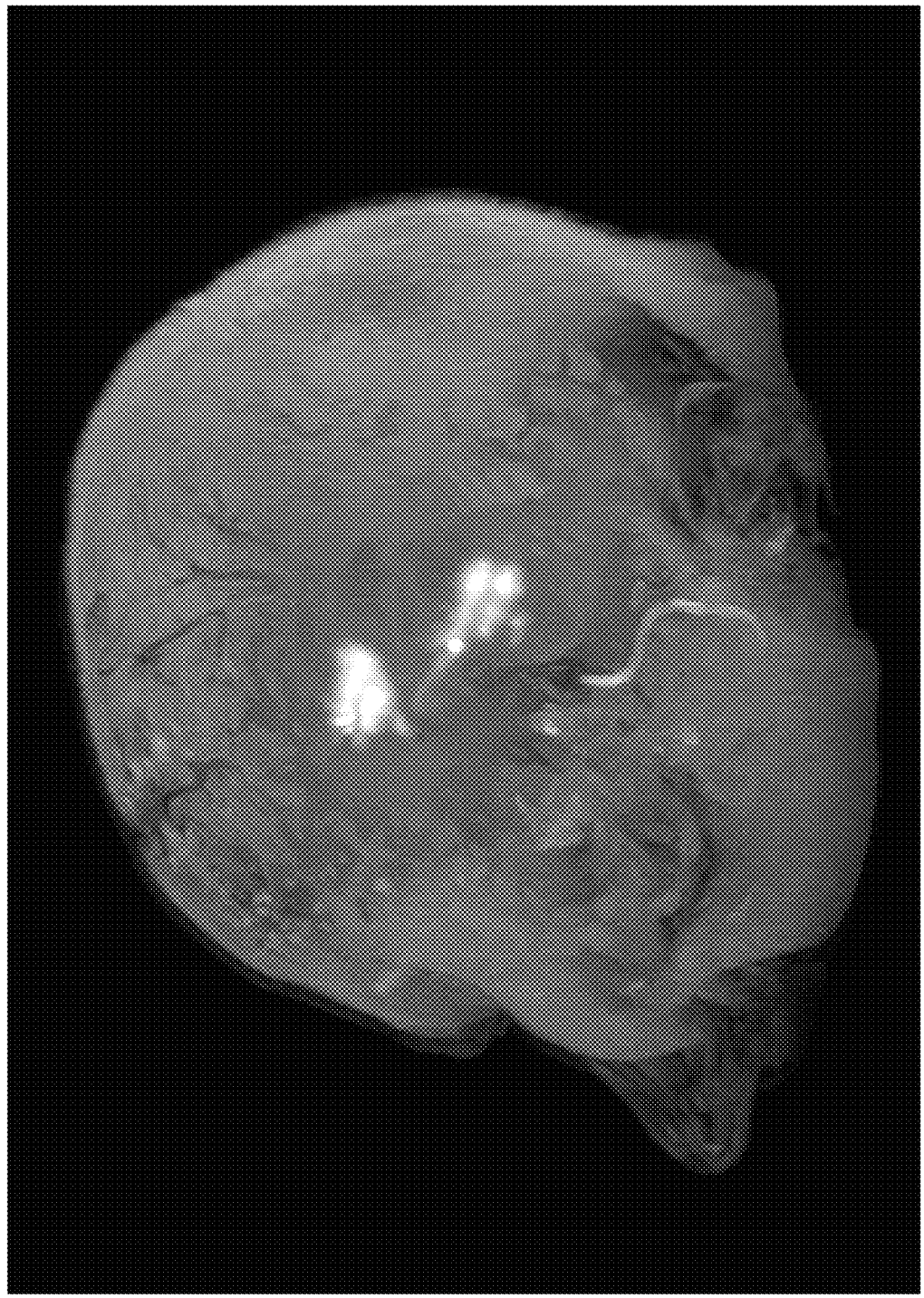
Figure 14:
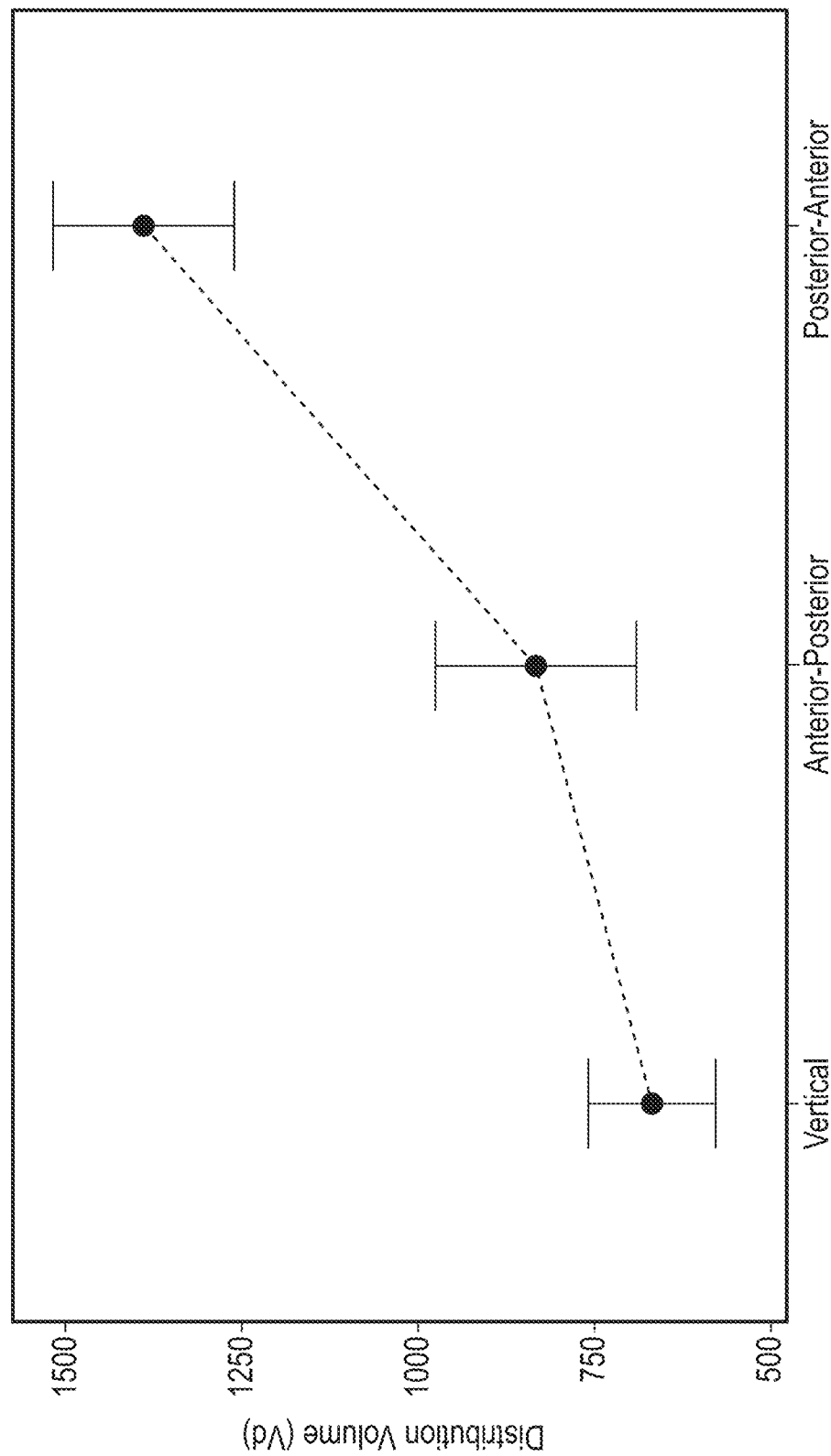
FIG. 14 shows the effect of trajectory on distribution volumes in the putamen as observed following 400 µl infusion volumes in human putamen (95% CI for the Mean).

The distribution volume was identified manually by assigning voxels of MRI scans to each catheter via a visual assessment and the results are shown in FIG. 14.

Figure 15:
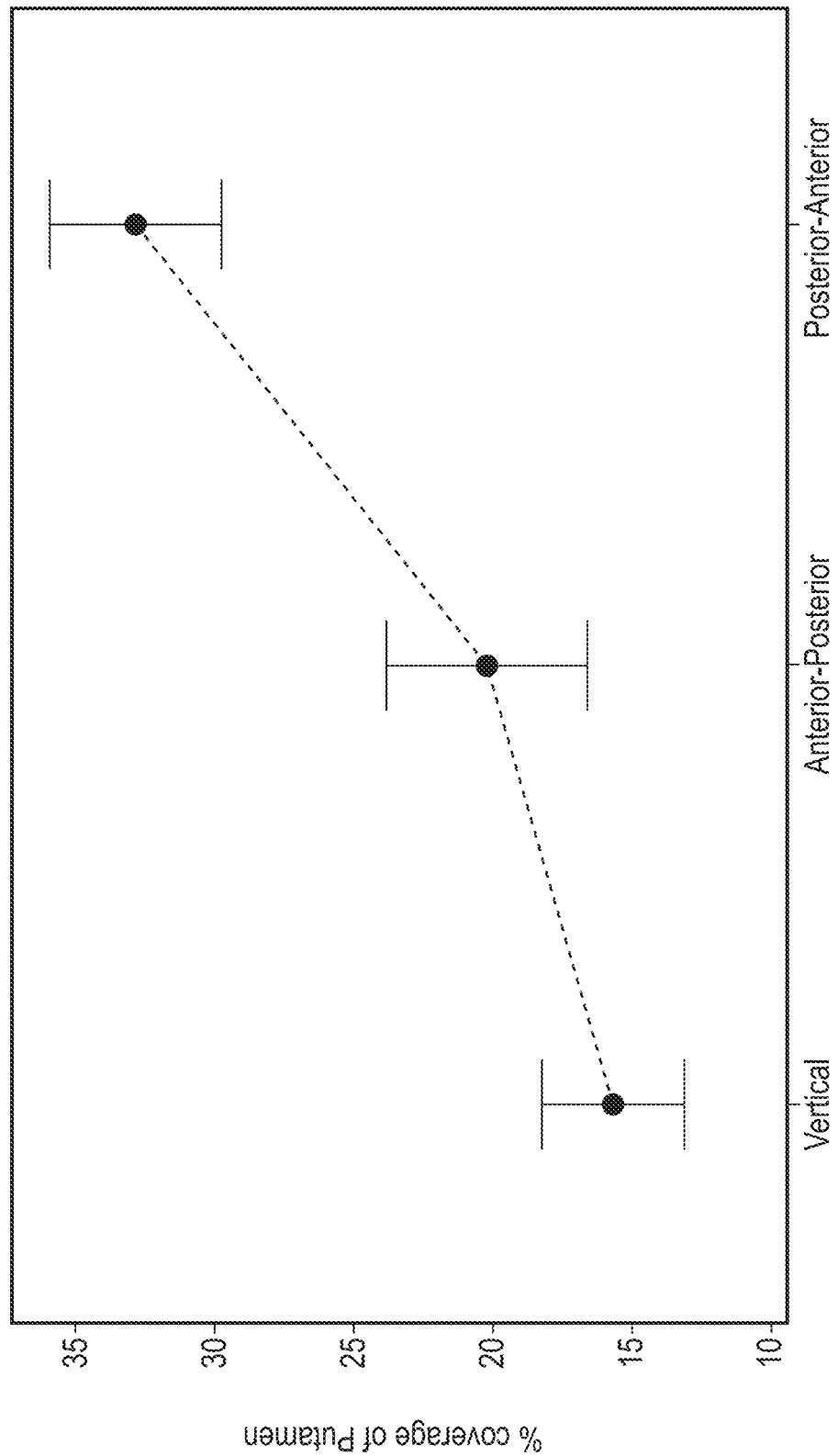
FIG. 15 shows the effect of trajectory on percentage coverage of Putamen (per catheter) and illustrates the percentage coverage observed directly relative to the size of each putamen into which the catheter was implanted. Data have not been normalised to account for differences in the volumes of each Putamen (95% CI for the Mean).

Percentages of coverage were calculated by dividing the volume of distribution by the volume of the putamen into which the infusion was targeted and are shown in FIG. 15.

Figure 16:
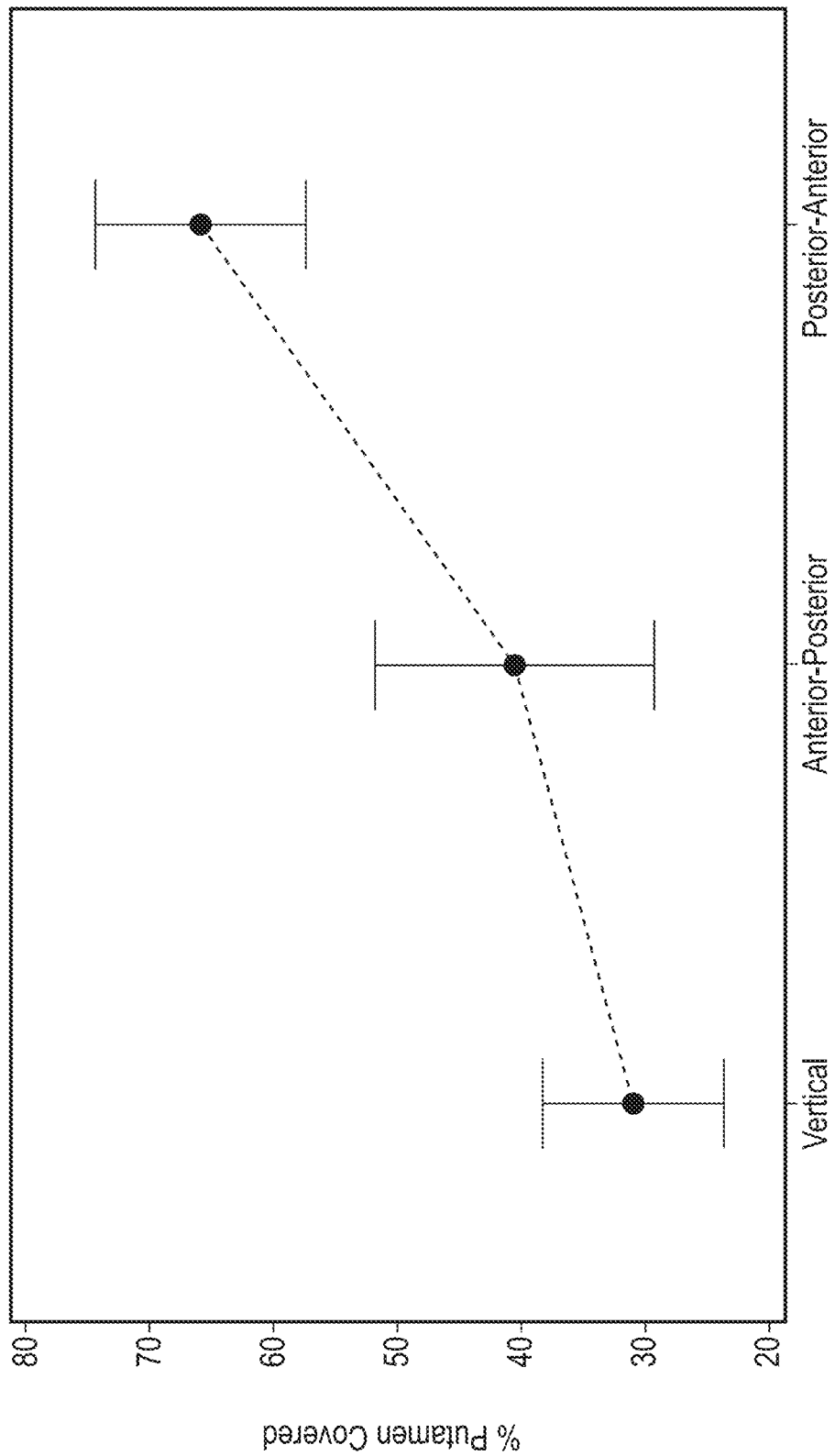
FIG. 16 shows the effect of trajectory on percentage coverage of putamen (per pair of catheters)—as in FIG. 15 but coverage following pairs of catheters are displayed (95% CI for the Mean).

Percentage coverage for pairs of catheters were assigned where two catheters infused into a single putamen, total distribution within the structure was then divided by the volume of the putamen and results are shown in FIG. 16.

As can be seen in the results, both the anterior to posterior and posterior to anterior approaches improved the volume of distribution over that achieved using the conventional vertical approach. However, surprisingly, while both the anterior to posterior and posterior to anterior approaches targeted the long axis of the putamen, the volume of distribution was significantly improved in the posterior to anterior approach. Without being bound by theory, the inventor believes that the angle of insertion needed to avoid the eye of a patient in an anterior to posterior approach leads to the reduced volume of distribution. A posterior to anterior approach allows the angle of insertion to be optimised, which improves the volume of distribution. This approach also has cosmetic benefits for patients as the catheter ports can usually be hidden under the patient's hair on the back of their head.

It will be appreciated that the above-disclosed features and functions, or alternatives thereof, may be desirably combined into different systems or methods. Also, various alternatives, modifications, variations or improvements may be subsequently made by those skilled in the art, and are also intended to be encompassed by the following claims. As such, various changes may be made without departing from the spirit and scope of this disclosure as defined in the claims.

REFERENCES

Barua N U, Lowis S P, Woolley M, O Sullivan S, Harrison R, Gill S S. Acta Neurochir (Wein). 2013 155:1459-65

Brady M L, Raghavan R, Alexander A, Kubota K, Sillay K and Emborg M E. Stereotact Funct Neurosurg 2013 91:69-78

Slevin J T, Herhardt G A, Smith C D, Gash D M, Kryscio R and Young B. J. Neurosurg. 2005 102:216-222

The invention claimed is:

1. A method for delivering a fluid to a brain of a subject, the method comprising delivering the fluid to the brain by inserting at least one intraparenchymal catheter into a target volume of the brain using a posterior to anterior approach along an insertion axis that is substantially aligned with a long axis of the target volume,
   wherein the target volume is at least one of the putamen, globus pallidus and the head of the caudate nucleus, and
   the catheter is inserted along a trajectory through an occipitoparietal region, the trajectory substantially parallel to an anterior commissure-posterior commissure plane.

2. The method of claim 1, wherein the trajectory is aligned with the long axis of the target volume to within 30° or less.

3. The method of claim 1, further comprising inserting at least a second intraparenchymal catheter into the target volume of the brain using the posterior to anterior approach.

4. The method of claim 1, wherein the subject is under general anaesthetic and in a prone position.

5. The method of claim 1, further comprising inserting at least a second intraparenchymal catheter into the target volume of the brain using the posterior to anterior approach, wherein the catheters are inserted bilaterally into the target volume of the brain.

6. A method for treating a neurodegenerative disorder, the method comprising delivering a fluid to a brain of a subject by inserting at least one intraparenchymal catheter into a target volume of the brain using a posterior to anterior approach along an insertion axis that is substantially aligned with a long axis of the target volume,
   wherein the target volume is at least one of the putamen, globus pallidus and the head of the caudate nucleus, and
   the catheter is inserted along a trajectory through an occipitoparietal region, the trajectory substantially parallel to an anterior commissure-posterior commissure plane.

7. The method of claim 6, wherein the neurodegenerative disorder is at least one of Multiple-System Atrophy, Progressive Supranuclear Palsy (PSP), Parkinson's Disease, Huntington's Disease, dystonia, tremor, Tourette's syndrome and lysosomal storage diseases.

8. The method of claim 6, wherein the trajectory is aligned with the long axis of the target volume to within 30° or less.

9. The method of claim 6, further comprising inserting at least a second intraparenchymal catheter into the target volume of the brain using the posterior to anterior approach.

10. The method of claim 6, wherein the subject is under general anaesthetic and in a prone position.

11. The method of claim 6, further comprising inserting at least a second intraparenchymal catheter into the target volume of the brain using the posterior to anterior approach, wherein the catheters are inserted bilaterally into the target volume of the brain.

12. A method for delivering a fluid to an elongate structure of a brain of a subject, the method comprising delivering the fluid to the elongate structure by inserting at least one intraparenchymal catheter having a step into the brain using a posterior to anterior approach along an insertion axis that is substantially aligned with a long axis of the elongate structure,
   wherein the step is located within the elongate structure,
   the elongate structure is at least one of the putamen, globus pallidus and the head of the caudate nucleus, and
   the catheter is inserted along a trajectory through an occipitoparietal region, the trajectory substantially parallel to an anterior commissure-posterior commissure plane.

13. The method according to claim 12, wherein the insertion axis is aligned with the long axis of the elongate structure to within 30° or less.

14. The method of claim 12, wherein the subject is under general anaesthetic and in a prone position.

15. The method of claim 12, wherein the fluid includes at least one therapeutic agent selected from the group consisting of a chemotherapy drug, a neurotrophin, an enzyme, a growth factor, an antibody, an immunotoxin, small inhibitory RNA (siRNA), antisense oligonucleotides, viral vectors, drug releasing nanoparticles, and transgenes.

* * * * *